(12) United States Patent
Shackelford et al.

(10) Patent No.: US 11,318,283 B1
(45) Date of Patent: May 3, 2022

(54) MEDICAL TUBE HOLDING APPARATUS

(71) Applicants: Sam L. Shackelford, Ruidoso, NM (US); Tyler Shackelford, Albuquerque, NM (US)

(72) Inventors: Sam L. Shackelford, Ruidoso, NM (US); Tyler Shackelford, Albuquerque, NM (US)

( * ) Notice: Subject to any disclaimer, the term of this patent is extended or adjusted under 35 U.S.C. 154(b) by 286 days.

(21) Appl. No.: 16/525,279

(22) Filed: Jul. 29, 2019

Related U.S. Application Data

(60) Provisional application No. 62/712,087, filed on Jul. 30, 2018.

(51) Int. Cl.
*A61M 25/02* (2006.01)

(52) U.S. Cl.
CPC ....... *A61M 25/02* (2013.01); *A61M 2025/022* (2013.01); *A61M 2025/024* (2013.01); *A61M 2025/028* (2013.01); *A61M 2025/0226* (2013.01); *A61M 2025/0253* (2013.01)

(58) Field of Classification Search
CPC ............ A61M 25/02; A61M 2025/022; A61M 2025/0206; A61M 2025/0213; A61M 2025/024; A61M 2025/0253; A61M 2025/028; A61M 2025/0226; A61M 16/0683; A61M 3/027
See application file for complete search history.

(56) References Cited

U.S. PATENT DOCUMENTS

| | | | | |
|---|---|---|---|---|
| 1,845,460 | A * | 2/1932 | Watters | A62B 18/02 |
| | | | | 128/201.15 |
| 3,602,227 | A * | 8/1971 | Andrew | A61M 25/02 |
| | | | | 128/207.17 |
| 3,760,811 | A * | 9/1973 | Andrew | A61M 25/02 |
| | | | | 128/207.17 |
| 3,774,616 | A | 11/1973 | White et al. | |
| 3,827,433 | A * | 8/1974 | Shannon | A61M 16/06 |
| | | | | 128/201.23 |
| 4,191,180 | A * | 3/1980 | Colley | A61M 16/0497 |
| | | | | 128/207.17 |

(Continued)

FOREIGN PATENT DOCUMENTS

| CA | 2166447 | 9/1999 |
|---|---|---|
| WO | 2015127443 A1 | 8/2015 |

OTHER PUBLICATIONS

"AnchorFast1", https://web.archive.org/web/20141218213244/www.anchorfast1.com/images/anchorfast.jpg, Dec. 18, 2014.

(Continued)

*Primary Examiner* — Nilay J Shah
(74) *Attorney, Agent, or Firm* — Peacock Law P.C.; Justin R. Muehlmeyer

(57) ABSTRACT

A medical tube holding system for holding tubes extending from the mouth of a patient. Embodiments of the system comprise a rim or mask shaped and sized to be supported on the face of a patient, a lower support surface comprising various shapes and openings, and a tube holding device comprising at least one opening for receiving a medical tube and comprising a first adjusting component and a second adjusting component. Embodiments of the system include various features, including adjusting mechanisms in various dimensions, tube clamps, cushioning and straps.

19 Claims, 4 Drawing Sheets

(56) References Cited

U.S. PATENT DOCUMENTS

| | | | |
|---|---|---|---|
| 4,326,515 A | | 4/1982 | Shaffer et al. |
| 4,331,143 A | * | 5/1982 | Foster ............... A61M 16/0488 128/207.14 |
| 4,378,012 A | | 3/1983 | Brown |
| 4,480,639 A | | 11/1984 | Peterson et al. |
| 4,537,192 A | * | 8/1985 | Foster ............... A61M 16/0488 128/207.14 |
| 4,707,906 A | | 11/1987 | Posey |
| 5,097,827 A | | 3/1992 | Izumi |
| 5,295,478 A | * | 3/1994 | Baldwin ........... A61M 16/0048 128/202.28 |
| 5,345,931 A | * | 9/1994 | Battaglia, Jr. ..... A61M 16/0488 128/207.17 |
| 5,437,273 A | | 8/1995 | Bates et al. |
| 5,490,504 A | * | 2/1996 | Vrona ............... A61M 16/0488 128/207.14 |
| 5,558,090 A | | 9/1996 | James |
| 5,643,174 A | | 7/1997 | Yamamoto et al. |
| 5,735,272 A | | 4/1998 | Dillon et al. |
| 5,755,225 A | | 5/1998 | Hutson |
| 6,029,668 A | | 2/2000 | Freed |
| 6,755,191 B2 | | 6/2004 | Bertoch et al. |
| 7,562,658 B2 | | 7/2009 | Madaus et al. |
| 8,302,597 B2 | | 11/2012 | Beely et al. |
| 8,974,382 B2 | | 3/2015 | Taljaard |
| 9,308,340 B2 | | 4/2016 | Bond et al. |
| 10,888,680 B2 | | 1/2021 | Zickefoose et al. |
| 2008/0294117 A1 | | 11/2008 | Ware |
| 2011/0240034 A1 | | 10/2011 | Ciccone |
| 2012/0168571 A1 | * | 7/2012 | Bond ................ A61M 16/0488 248/70 |
| 2012/0227747 A1 | * | 9/2012 | Levine ............. A61M 16/0493 128/207.14 |
| 2014/0261462 A1 | * | 9/2014 | Visconti ................ A61M 25/02 128/861 |
| 2014/0261463 A1 | * | 9/2014 | Visconti ............ A61M 16/0497 128/861 |
| 2016/0339194 A1 | * | 11/2016 | Molden ............. A61M 16/0493 |
| 2017/0197049 A1 | | 7/2017 | Doll |
| 2019/0388303 A1 | | 12/2019 | Sharaiha |
| 2020/0222651 A1 | | 7/2020 | Jockel et al. |
| 2021/0008315 A1 | | 1/2021 | Drew et al. |
| 2021/0128860 A1 | | 5/2021 | Van Der Vegt et al. |

OTHER PUBLICATIONS

"AnchorFast Guard", https://www.hollister.com/en/products/critical-care-products/tube-securement/endotracheal-tube-fasteners/anchorfast-guard-oral-endotracheal-tube-fastener, Feb. 23, 2016.

"AnchorFastl", https://web.archive.org/web/20141218213244/www.anchorfast1.com/images/anchorfast.jpg, Dec. 18, 2014.

"Marpac 320, Adjustable ET Tube Holder, Patent Pending", https://www.youtube.com/watch?v=ZgxwPekeiLg, Sep. 8, 2011.

"Photograph provided by inventor", Source unknown, Nov. 3, 2017.

Reichman, E F, "Emergency Medical Procedures", https://accessemergencymedicine.mhmedical.com/Content.aspx?bookid=6838sectionid=45343703, 2017.

* cited by examiner

MEDICAL TUBE HOLDING APPARATUS

CROSS-REFERENCE TO RELATED APPLICATIONS

This application claims priority to and the benefit of U.S. Provisional Patent Application No. 62/712,087, entitled "Medical Tube Holding Mask", filed on Jul. 30, 2018, and the specifications and claims thereof are incorporated herein by reference.

BACKGROUND OF THE INVENTION

Field of the Invention (Technical Field)

Embodiments of the present invention relate to medical tube retaining apparatuses, and more particularly, to apparatuses for holding medical tubes extending from the mouth of a patient, such as a gastric tube, in position during extended care of a patient in need thereof.

Description of Related Art

There are very few commercially available holders for medical tubes extending from the mouth or nose of a patient, so medical practitioners have to be creative and improvise to hold these tubes in place. In the case of gastric balloon inflation medical tubes that must stay in place for extended periods of time, sometimes they will attach a rod to a helmet, or use a football helmet with a bar across the face area, or use a baseball catcher's face mask and tape the tube in place. Other devices wrap around the patient's face and/or stick to their face while holding the tube with a plastic zip tie. The issue with these solutions is that they fail to properly hold the tubes in place, produce discomfort for the patient after a while, and sometimes they even cause pressure sores during extended care.

Embodiments of the present invention alleviate these problems by providing masks to support medical tubes comprising a cushioned rim to be disposed over the patient's face. In one embodiment, the cushioning is divided into various segments to be changed in configuration around the face of the patient and avoid extended pressure in a single place. One embodiment further comprises a peripheral rim with a support that goes over the patient's lower face/mouth, below the nose and is preferably elevated higher than the level of the patient's nose so that it does not touch the patient's face. In one embodiment, the support comprises an opening at the chin area for convenient removal/placement of the medical tube, and an adjustable clamping mechanism for holding the tube in place and exerting linear outward pressure to the tube to remain in place.

BRIEF SUMMARY OF THE INVENTION

Embodiments of the present invention relate to an apparatus for holding medical tubes extending from the mouth of a patient, the apparatus comprising: a rim; a lower support surface disposed on the rim, the lower support surface shaped to extend at least partially over a portion of the patient's face below the patient's nose; a tube holding device disposed on the lower support surface, the tube holding device comprising at least one opening for receiving a medical tube and comprising a first adjusting component and a second adjusting component. The rim can be a cylindrical or tubular object, can be shaped to partially encircle the patient's face, can be shaped similar to the shape of a horseshoe, can comprise a circular shape, an oval shape, can comprise an outward projection, can comprise a first plane at a first elevation and a second plane at a second elevation above the first plane, and can comprise cushioning. The lower support surface can comprise a dome shape, an opening, rails, a lateral slit, and/or transparent material. The first adjusting component can comprise rails or slots that coordinate with rails on the lower support surface. The second adjusting component can comprise clamps to secure the medical tubes and/or vertical adjusting guides to adjust the depth of the tubes relative to the patient's mouth.

Embodiments of the present invention also relate to an apparatus for holding a medical tube extending from the mouth of a patient comprising: a mask sized to at least partially extend over the face of a patient; a tube holding device disposed on the mask, the tube holding device comprising at least one opening for receiving a medical tube and comprising a first adjusting component and a second adjusting component. The first adjusting component can be adjustable in a dimension that is coplanar with the plane of the mask, and the second adjusting component can be adjustable in a dimension that is in an intersecting plane with the plane of the mask.

Embodiments of the present invention also relate to a method of holding a medical tube extending from the mouth of a patient comprising: securing a mask sized to at least partially extend over the face of a patient, the mask comprising a tube holding device disposed on the mask, the tube holding device comprising at least one opening for receiving a medical tube and comprising a first adjusting component and a second adjusting component; adjusting a first position of the medical tube by adjusting the first adjusting component, the first position in a dimension that is coplanar with the plane of the mask; adjusting a second position of the medical tube by adjusting the second adjusting component, the second position in a dimension that is in an intersecting plane with the plane of the mask.

Objects, advantages and novel features, and further scope of applicability of the present invention will be set forth in part in the detailed description to follow, and in part will become apparent to those skilled in the art upon examination of the following, or may be learned by practice of the invention.

BRIEF DESCRIPTION OF THE SEVERAL VIEWS OF THE DRAWINGS

The accompanying drawings, which are incorporated into and form a part of the specification, illustrate one or more embodiments of the present invention and, together with the description, serve to explain the principles of the invention. The drawings are only for the purpose of illustrating one or more embodiments of the invention and are not to be construed as limiting the invention. In the drawings.

DETAILED DESCRIPTION OF THE INVENTION

In the following detailed description, numerous specific details are set forth in order to provide a thorough understanding of the embodiments of the invention. However, it will be understood by one of ordinary skill in the art that the embodiments may be practiced without these specific details. For instance, well known operation or techniques may not be shown in detail, Technical and scientific terms used in this description have the same meaning as commonly understood to one of ordinary skill in the art to which this subject matter belongs.

Figure 1:
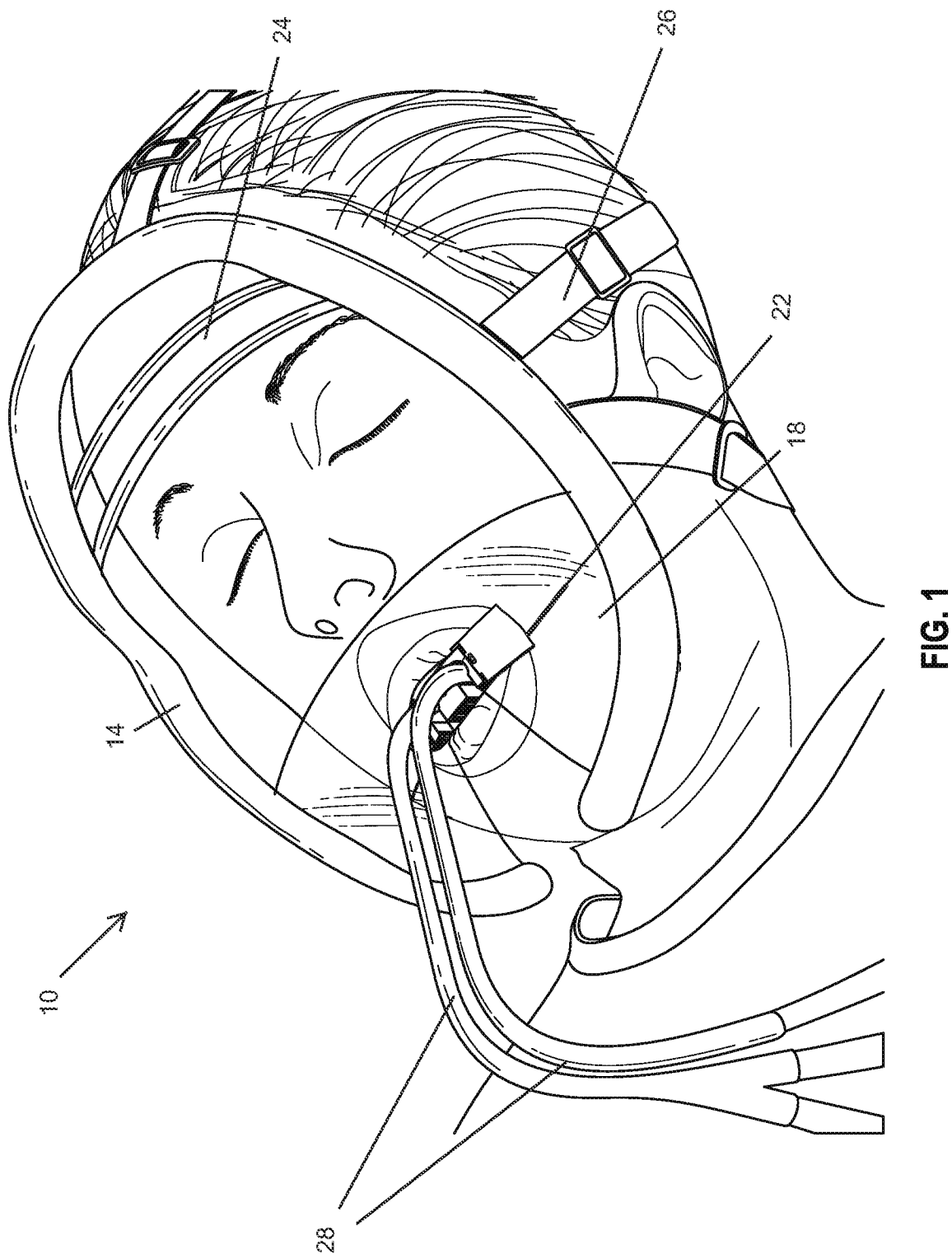
FIG. 1 is a perspective view of a medical tube holding mask according to an embodiment of the present invention.
Figure 2:
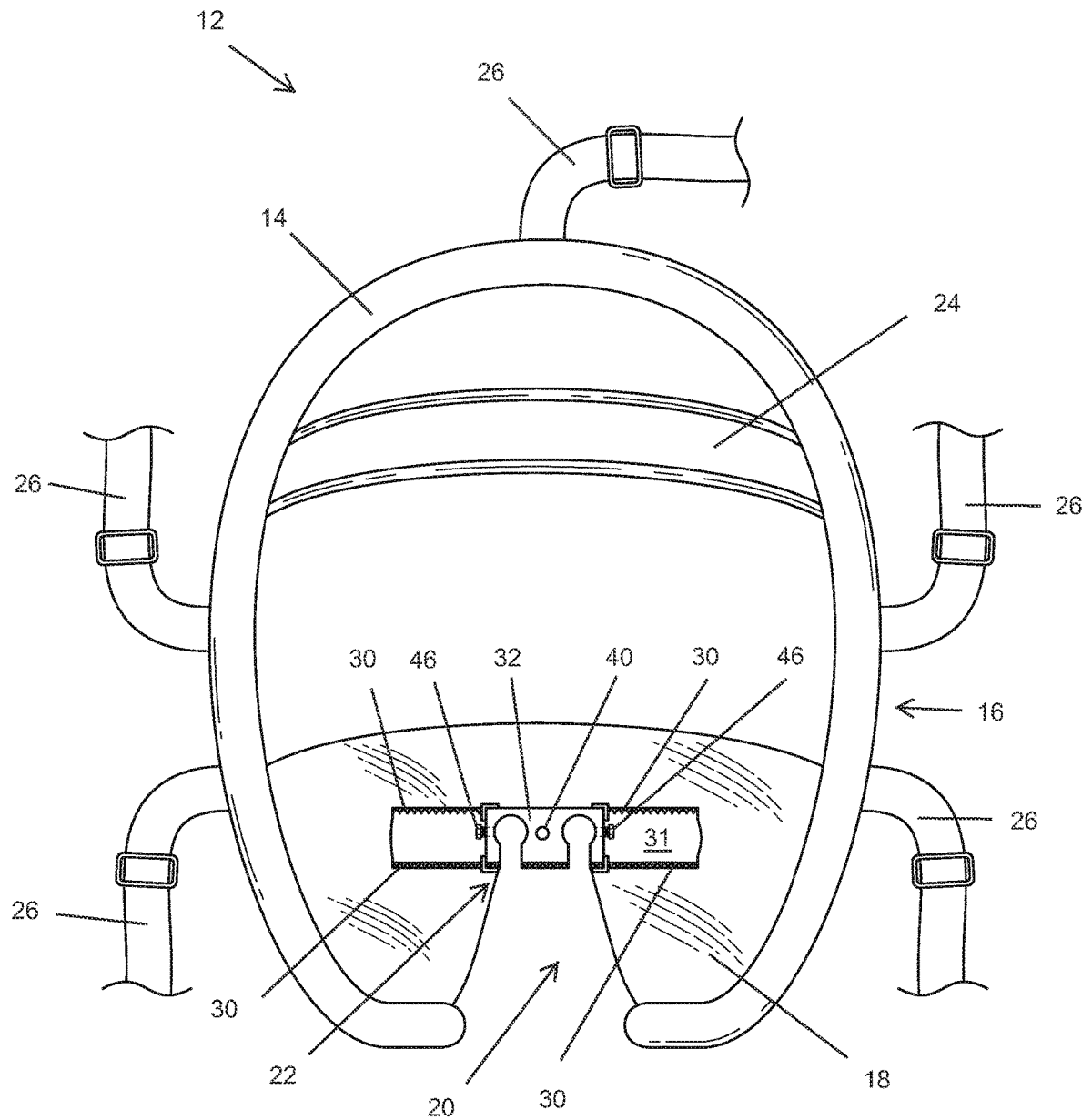
FIG. 2 is a front view of a medical tube holding mask according to the present invention.

Referring now to the Figures, and more particularly to FIGS. 1-2, there is shown medical tube holding system 10 comprising mask 12. In one embodiment, mask 12 comprises rim 14. Rim 14 is preferably an object shaped and sized to follow the outline and/or contour of the patient's face without obstructing or covering the patient's entire face, for example as depicted in the figures. In this way, other objects can be supported over the patient's face without interfering significantly with visibility or accessibility to the face by either the patient or the doctor. As illustrated in FIG. 1, rim 14 is preferably a cylindrical or tubular object partially encircling the patient's face and/or generally shaped as the shape of the outline of the patient's face. In the embodiment illustrated, the shape is similar to the shape of a horseshoe with some three-dimensional aspects that give the rim 14 contour by projecting outward from the patient's face like a dome. For purposes of aiding the discussion of the shape of rim 14, one can make reference to the plane of rim 14. In the case of the mask 12 depicted in FIG. 2 in which rim 14 is depicted flat without any projections, the plane of rim 14 would simply be the plane of the paper on which FIG. 2 is drawn. The outward projection of rim 14 illustrated in FIG. 1 aids in elevating other parts of rim 14 away from the patient's face, for example as discussed below to elevate tube holding device 22 away from the patient's face. In this sense, the rim 14 of FIG. 1 that has an outward projection then has at least two planes, a first plane that corresponds to the forehead area of the patient and a second plane that is higher in elevation than the first plane and that corresponds to the lower part of the patient's face, including the nose and mouth area.

Note that rim 14 may vary in shape according to the application of the apparatus, for example if the apparatus is intended to be used with an animal, or a child or baby as compared to an adult. Embodiments of rim 14 can be of other shapes, for example, linear, rectangular, circular, triangular, etc., or some combination of those shapes. For example, rim 14 could be rectangular on its lower portion and circular on its upper portion. In another example for a long face like a dog or horse, rim 14 may form a number of planes that are at more extreme angles to each other than the rims 14 depicted in the illustrations. In some embodiments, rim 14 itself is not tubular or cylindrical but is flat. In some embodiments, rim 14 also encircles or extends over the patient's head rather than only their face. Rim 14 is preferably constructed of a material that holds its structure well and that can be supported by a patient's face without harm or pain, for example, plastic, Styrofoam, stainless steel, etc.

Rim 14 is preferably disposed on the patient's face in direct contact with the face. The side of rim 14 in contact with the patient or closest to patient can be referred to as the "bottom" side of the rim as opposed to the side that is farthest from the patient which can be referred to as the "top" of the rim. To support rim 14 on the patient's face securely and comfortably, rim 14 preferably comprises cushioning 16. Preferably, cushioning 16 of rim 14 is divided into various sections to be changed in configuration around the face of the patient and avoid extended pressure in a single place. In some embodiments, cushioning 16 is disposed only on rim 14 on the bottom side of the rim at certain points of contact with the patient's face. Cushioning 16 may comprise structures of its own, for example, protrusions, extensions, projections, etc, and/or simply be continuous with the shape of rim 14 and/or be of the same material as rim 14. For example, in some embodiments rim 14 is shaped to extend or with projections that extend outward from the plane of rim 14 to the patient's face. The particular shapes and locations of the projections on rim 14 may vary to accommodate the particular contours of the patient's face at the location of the projection.

Mask 12 preferably further comprises lower support surface 18 to support tube holding device 22 over the patient's mouth. In an embodiment illustrated in FIG. 1, tube holding device 22 is preferably a clamping mechanism disposed over the patient's lower face/mouth, below the nose, and elevated higher than the level of the patient's nose. In one embodiment, lower support surface 18 curves in a dome shape outward from the plane of rim 14. Preferably, lower support surface 18 comprises opening 20 at the chin area of the patient's face for convenient removal/placement of the medical tubes, and tube holding device 22 for holding one or more medical tubes 28 in place.

In another embodiment, mask 12 comprises a lateral slit comprising grooved rails 30 embedded within the sides of the slit for adjusting the lateral position of tube holding device 22. The slit 31 may take other orientations as well. For purposes of aiding the discussion of the orientation of various objects on medical tube holding system 10, one can make reference to the upper portion of mask 12 as the part that would correspond with the patient's forehead, the lower portion as the part that would correspond with the lower part of the patient's face (the jaw or mouth), and a first and second side that would correspond with the patient's left and right ears. Slit 31 as illustrated in FIGS. 1-2 has a primary axis (meaning an axis along its length) that is parallel with the axis formed by the line between the patient's ears. In that sense, slit 31 is considered "lateral". In other embodiments, slit 31 may have a vertical orientation, that is, the primary axis of slit 31 is parallel with the axis formed by the line between the patient's nose and mouth.

Various other objects are preferably used to help secure mask 12 to the patient's face. For example, in another embodiment, mask 12 further comprises upper support 24, which preferably curves outward in a dome shape and provides rigidity to mask 12. In a preferred embodiment, mask 12 comprises one or more holding straps 26 for placement over the patient's head. Preferably, lower support surface 18 and upper support 24 are made of a transparent material to improve visibility of the patient's face.

Referring to FIGS. 3-6, there is shown a closer and more detailed view of an adjustable tube holding device according to an embodiment of the present invention. Preferably, tube holding device 22 comprises at least one dimension of adjustability so that the medical tubes can be properly adjusted according to the needs of the patient. Preferably, tube holding device 22 comprises a first adjusting component and a second adjusting component that are oriented one on top of the other so that they stack in a direction that is outward from the plane of rim 14.

In one embodiment, tube holding device 22 comprises top adjusting component 32 and bottom adjusting component 34. Preferably, the bottom adjusting component 34 adjusts the lateral orientation of tube holding device 22. Preferably bottom adjusting component 34 is configured to be laterally adjustable for changing the positioning of the medical tubes from one side of the patient's mouth to the other side. This lateral adjustment is preferably accomplished by a railing system. In one embodiment, lower support surface 18 comprises grooved rails 30 that coordinate with bottom adjusting component 34. This may be accomplished, for example, by providing slots 36 on the sides of bottom adjusting component 34 that interlock or otherwise coordinate with grooved rails 30. In one embodiment, the sides of bottom adjusting component 34 with slots 36 and grooved rails 30 are angled inwards at their bottom sides (see FIG. 6), which allows them to lock in place at a desired lateral position (see FIG. 2). In this embodiment, a user can move tube holding device 22 by snapping in and out the angled slots of bottom adjusting component 34 along the grooved rails as needed. In another embodiment, bottom adjusting component 34 comprises projections or shapes that coordinate with rails 30 or may be laterally adjustable with lower support surface 18 using snapping mechanisms, latching mechanisms, sliding mechanisms, etc.

Figure 3:
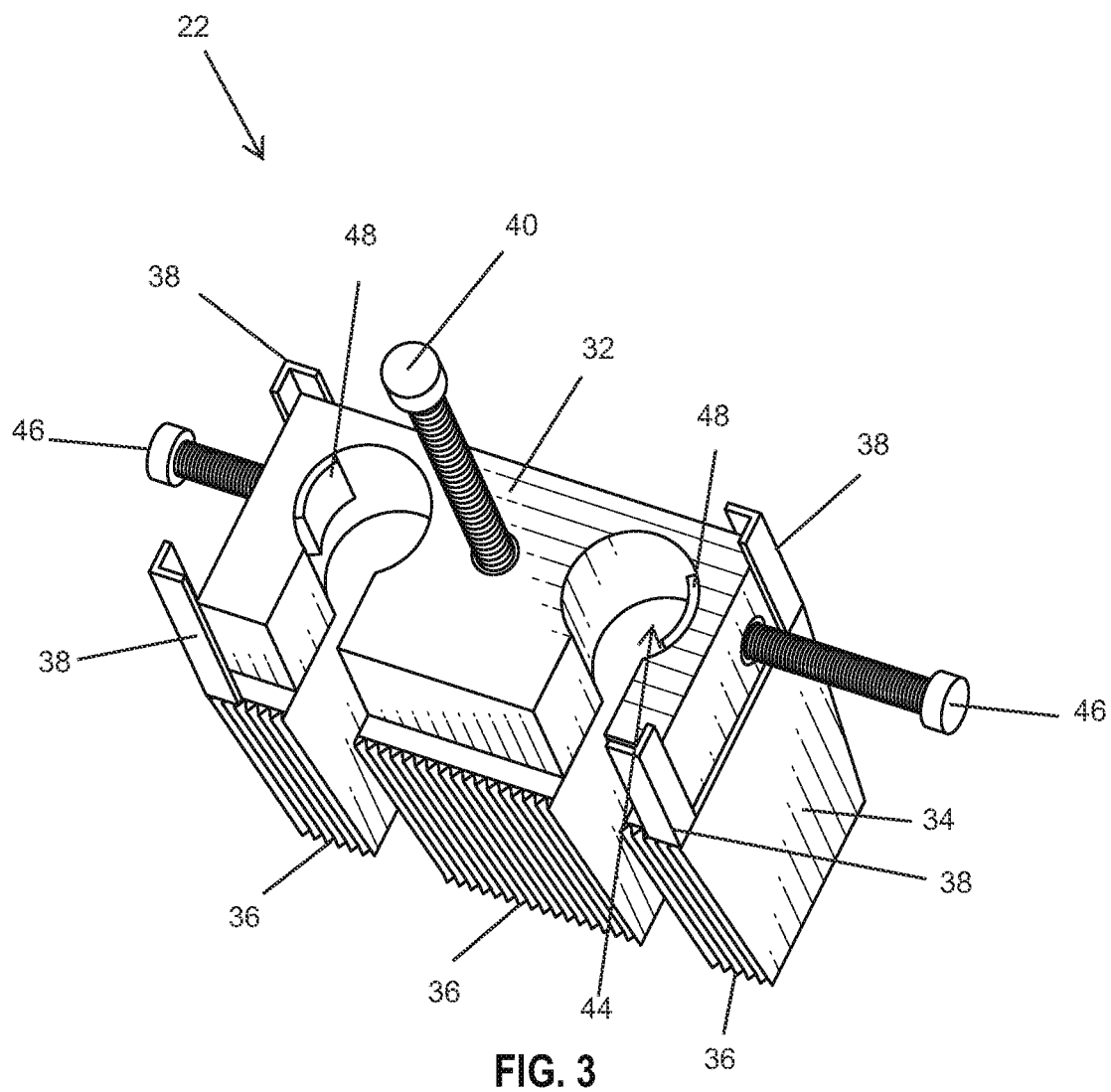
FIG. 3 is a perspective view of an adjustable medical tube clamping system comprising a two-component riding block according to an embodiment of the present invention.
Figure 4:
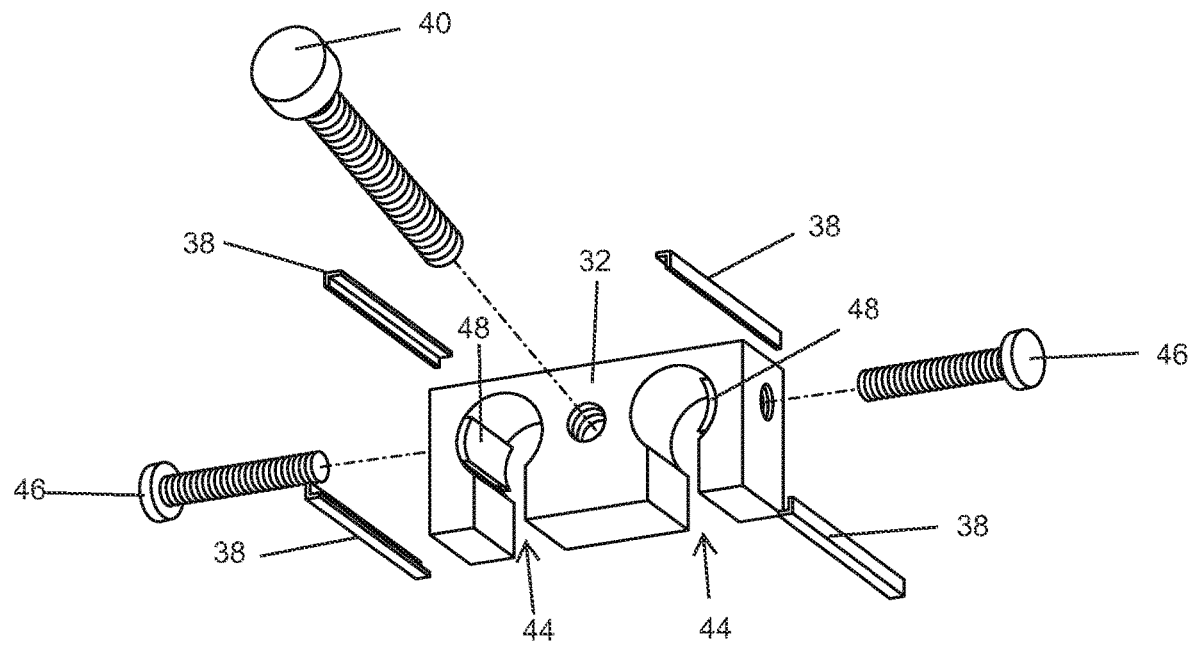
FIG. 4 is an exploded view of the top component of the riding block embodiment of FIG. 3.
Figure 5:
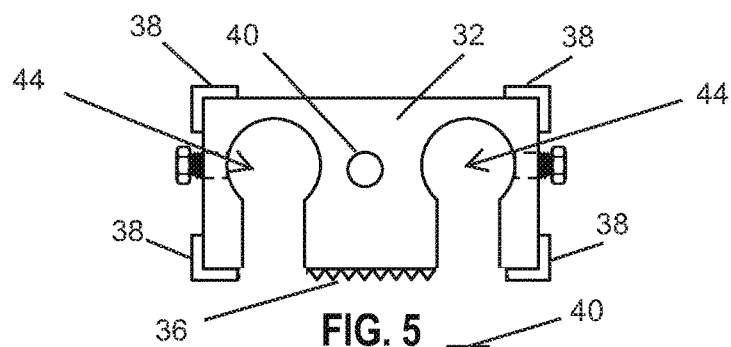
FIG. 5 is a top view of the two-component riding block of FIG. 3.
Figure 6:
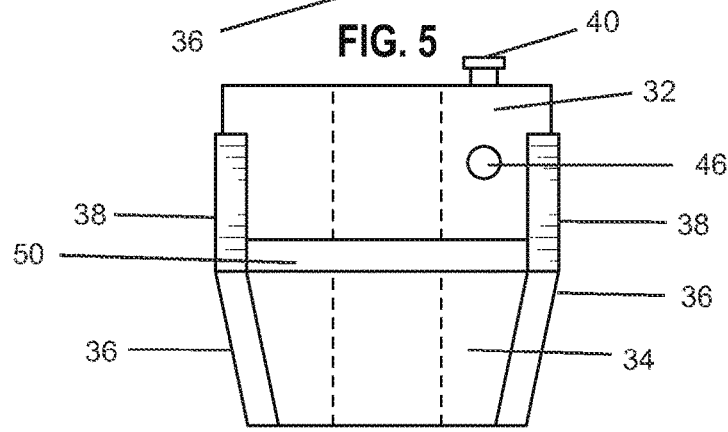
FIG. 6 is a side view of the two-component riding block of FIG. 3.

Preferably, the top adjusting component adjusts the vertical orientation of tube holding device 22 and comprises clamps. In an embodiment illustrated in FIGS. 3-4, top adjusting component 32 comprises tube placement openings 44 and screws 46 comprising movable plate jaws 48 for adjustably clamping the medical tubes. In a preferred embodiment, screws 46 attach to movable plate jaws 48 such that movable plate jaws 48 can swivel as screws 46 are turned so that the jaws advance and can clamp the tubes without spinning or changing the orientation of movable plate jaws 48. Referring to FIG. 3, the shape of movable plate jaws 48 comprises a curved shape to coordinate with or match the cylindrical shape of the medical tube and prevent puncturing of it. Movable plate jaws 48 may be shaped in ways other than as depicted in the figures. For example, in another embodiment, movable plate jaws 48 comprise a soft material for contacting the medical tubes, for example a square, cube, circle, cylinder or cone.

Preferably, in addition to clamping the medical tubes, tube holding device 22 is also capable of adjusting the internal positioning of the ends of the medical tubes, for example in the case of an inflatable gastric tube, by exerting linear outward pressure so that the tube can remain in place after being inflated inside the patient, or in another specific desired position for other types of medical tubes. In one embodiment, top adjusting component 32 is adjusted up and down along slide guides 38 with, for example, screw 40. For purposes of aiding the discussion of the orientation of various objects on medical tube holding system 10, one can make reference to the plane of mask 12 just as described elsewhere in this application with the plane of rim 14, and anything moving in a direction generally within that plane, and reference to an object moving within an intersecting plane, for example an object that is moving outward away from mask 12 or inward approaching the face of the patient. Slide guides 38 are preferably attached to bottom adjusting component 34 and directed in a manner such that top adjusting component 32 can coordinate with slide guides 38 to adjust up and down in a direction that would be intersecting the plane of mask 12. With this embodiment, a user can place, for example, a deflated inflatable gastric tube into the patient, inflate it, and then adjust the position of the inflated tube by increasing or decreasing separation 50 between the top adjusting component 32 and bottom adjusting component 34 (see FIG. 6) as screw 40 turns up or down.

Other embodiments for tube holding devices include, but are not limited to, for example, spring type (wherein a spring exerts linear outward pressure so that the tubes remain in place inside the patient); locking strap type; ratchet squeeze type, etc.

Although various dimensions of embodiments of the present invention are described and illustrated, the use of such dimensions is merely intended to provide the reader with the most preferred embodiment of the invention—to be clear, such dimensions are not essential to the operation of the invention and one or more, or even all, of the dimensions can be changed and will provide desirable results.

Note that in the specification and claims, "about" or "approximately" means within twenty percent (20%) of the numerical amount cited. Although the invention has been described in detail with particular reference to these embodiments, other embodiments can achieve the same results, Variations and modifications of the present invention will be obvious to those skilled in the art and it is intended to cover in the appended claims all such modifications and equivalents. The entire disclosures of all references, applications, patents, and publications cited above are hereby incorporated by reference.

What is claimed is:

1. An apparatus for holding a medical tube extending from a patient's mouth, the apparatus comprising:
 a rim;
 a lower support surface having a top and a bottom, said lower support surface disposed on said rim, said lower support surface shaped to extend at least partially over a portion of the patient's face below the patient's nose, said lower support surface comprising a slit, the slit laterally oriented on said lower support surface and also extending to the bottom of said lower support surface;
 a tube holding device disposed on said lower support surface within said slit, said tube holding device comprising at least one opening for receiving the medical tube, wherein said opening extends to the bottom of said tube holding device, and wherein said tube holding device further comprising a first screw, the first screw disposed to advance into the opening, wherein said first screw comprises a plate jaw disposed on said first screw and within said opening.

2. The apparatus of claim 1 wherein the tube holding device comprises a first adjusting component and a second adjusting component, wherein said first adjusting component is adjustable along said lower support surface, and wherein said second adjusting component comprises the first screw.

3. The apparatus of claim 2 wherein the second adjusting component comprises a second screw capable of adjusting said second adjusting component in a direction that is intersecting said lower support surface and in a direction away from said first adjusting component.

4. The apparatus of claim 3 wherein said first adjusting component comprises at least one slide guide disposed on a top of the first adjusting component and extending above said second adjusting component.

5. The apparatus of claim 2 wherein said second adjusting component is disposed on top of said first adjusting component.

6. The apparatus of claim 2 wherein said second adjusting component comprises a vertical adjusting guide.

7. The apparatus of claim 1 wherein said rim is a tubular object.

8. The apparatus of claim 1 wherein said rim is shaped to partially encircle the patient's face.

9. The apparatus of claim 1 wherein said rim comprises a horseshoe shape.

10. The apparatus of claim 1 wherein said rim comprises an oval shape.

11. The apparatus of claim 1 wherein said rim projects outwardly at a lower portion.

12. The apparatus of claim 1 wherein said rim comprises a first plane at a first elevation and a second plane at a second elevation above said first plane.

13. The apparatus of claim 1 wherein said rim further comprises cushioning.

14. The apparatus of claim 1 wherein said lower support surface comprises a dome shape.

15. The apparatus of claim 1 wherein said lower support surface comprises a transparent material.

16. The apparatus of claim 1 wherein said tube holding device comprises a first rail, and wherein said lower support surface comprises a second rail capable of coordinating with said first rail and disposed at or near said slit.

17. An apparatus for holding a medical tube extending from a patient's mouth, the apparatus comprising:
   a mask sized to at least partially extend over the patient's face, the mask comprising a slit, the slit laterally oriented on a lower support surface and also extending to the bottom of said lower support surface;
   a first rail disposed at or near said slit;
   a tube holding device disposed on said mask within said slit, said tube holding device comprising at least one opening for receiving a medical tube, wherein the opening extends to the bottom of said tube holding device, and wherein said tube holding device further comprises a first screw, the first screw disposed to advance into the opening, wherein said first screw comprises a plate jaw disposed on said first screw and within said opening.

18. The apparatus of claim 17 wherein the tube holding device comprises a first adjusting component and a second adjusting component, wherein said first adjusting component is adjustable along said lower support surface, and wherein said second adjusting component comprises the first screw, and wherein the second adjusting component comprises a second screw capable of adjusting said second adjusting component in a direction that is intersecting said lower support surface and in a direction away from said first adjusting component.

19. A method of holding a medical tube extending from a patient's mouth comprising:
   securing a mask sized to at least partially extend over the patient's face, the mask comprising a slit, the slit laterally oriented on the mask and also extending to the bottom of the mask, the mask comprising a tube holding device disposed on the mask, the tube holding device comprising at least one opening for receiving the medical tube, the opening extending to the bottom of the tube holding device, and the tube holding device comprising a first screw, the first screw disposed to advance into the opening;
   adjusting a first position of the medical tube by adjusting the tube holding device within the slit;
   adjusting the medical tube by loosening the first screw.

* * * * *